(12) United States Patent
Tasci

(10) Patent No.: US 10,383,653 B2
(45) Date of Patent: Aug. 20, 2019

(54) SYSTEM FOR EXCISING ANAL FISTULA TRACES

(71) Applicant: Ihsan Tasci, Istanbul (TR)

(72) Inventor: Ihsan Tasci, Istanbul (TR)

( * ) Notice: Subject to any disclaimer, the term of this patent is extended or adjusted under 35 U.S.C. 154(b) by 151 days.

(21) Appl. No.: 14/900,341

(22) PCT Filed: Jun. 23, 2014

(86) PCT No.: PCT/TR2014/000231
§ 371 (c)(1),
(2) Date: Dec. 21, 2015

(87) PCT Pub. No.: WO2014/204420
PCT Pub. Date: Dec. 24, 2014

(65) Prior Publication Data
US 2016/0143656 A1 May 26, 2016

(30) Foreign Application Priority Data

Jun. 22, 2013 (TR) ................. 2013/07559

(51) Int. Cl.
*A61B 17/3205* (2006.01)
*A61B 17/00* (2006.01)
(Continued)

(52) U.S. Cl.
CPC .... *A61B 17/3205* (2013.01); *A61B 17/00234* (2013.01); *F16C 1/06* (2013.01);
(Continued)

(58) Field of Classification Search
CPC ...... A61B 2017/00314; A61B 17/3205; A61B 17/00234; A61B 2017/00398;
(Continued)

(56) References Cited

U.S. PATENT DOCUMENTS

| | | | |
|---|---|---|---|
| 2009/0171147 A1* | 7/2009 | Lee | A61B 17/29 600/104 |
| 2011/0144673 A1 | 6/2011 | Zhang | |

(Continued)

FOREIGN PATENT DOCUMENTS

WO 02/083012 A 10/2002

*Primary Examiner* — Todd J Scherbel
*Assistant Examiner* — Brooke Labranche
(74) *Attorney, Agent, or Firm* — Preston Smirman; Smirman IP Law, PLLC

(57) ABSTRACT

Current invention relates to a combined system developed for the purpose of use in the treatment of anorectal fistulas. Fistulectomy Set is a system consisting of fistulectomy units which functions fully controlled and transmitting the pivoted movement which comes from the movement providing and transmitting part to the cutting edge by moving it on a central guide with the help of a motion carrier flexible shaft consisting of hexahedron spheroid parts. It consists of a cannulation apparatus which provides a simultaneous rotation, vibration and reciprocating movement and which detects the fistula trace fully and accurately. With this cutting edge, a channel surrounded by living tissue is obtained by cutting around the fistula trace cylindrically with suitable thickness, and thus cutting the secretory mucosa, dead tissues and fibrotic structures. With the developed system, it is believed that important progress will be made in the treatment of anorectal fistula; an important social and medical problem. It will prevent the loss of labor force, shorten hospital stays, reduce costs and minimize complications of treatment. Most importantly, it will prevent anal incontinence and hence a very important problem will be solved.

11 Claims, 15 Drawing Sheets

(51) Int. Cl.
*F16C 1/06* (2006.01)
*A61B 17/32* (2006.01)
(52) U.S. Cl.
CPC .............. *A61B 2017/00314* (2013.01); *A61B 2017/00398* (2013.01); *A61B 2017/00641* (2013.01); *A61B 2017/00734* (2013.01); *A61B 2017/32006* (2013.01)
(58) Field of Classification Search
CPC ........... A61B 2017/00641; A61B 2017/32006; A61B 2017/00734; A61F 2002/9583; F16C 1/06
See application file for complete search history.

(56) References Cited

U.S. PATENT DOCUMENTS

| | | | | |
|---|---|---|---|---|
| 2014/0187338 A1* | 7/2014 | Chen | ................... | F16D 3/18 464/158 |
| 2015/0314112 A1* | 11/2015 | Griffith | ................ | A61M 27/00 604/540 |

* cited by examiner

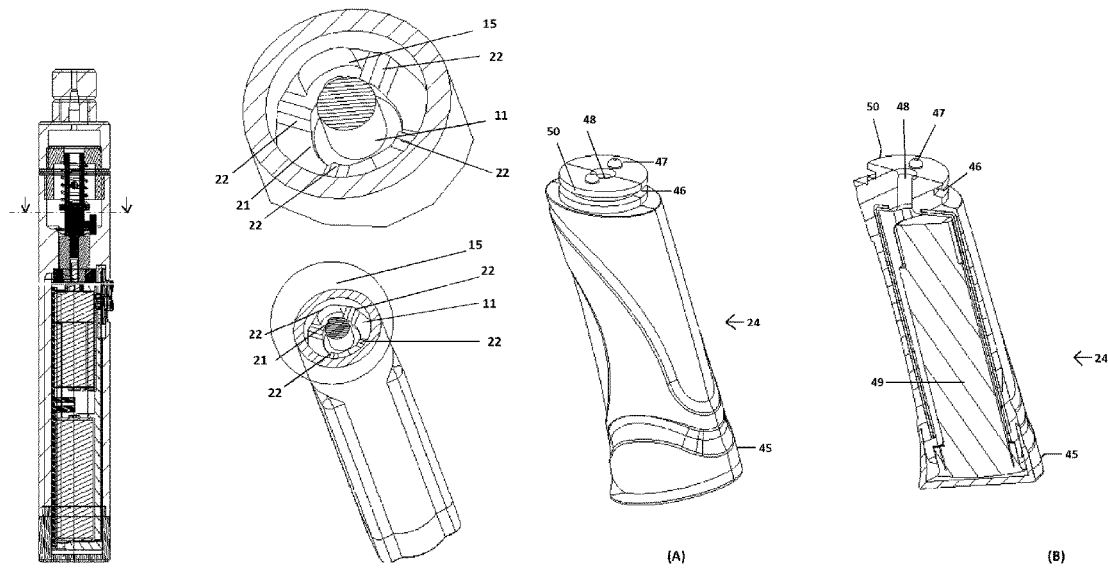
Figure 4
Figure 10
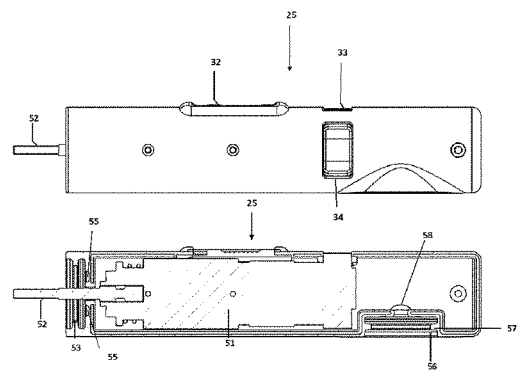
Figure 11
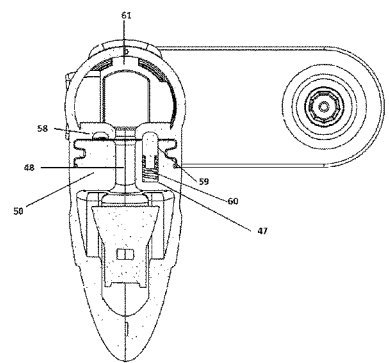
Figure 12
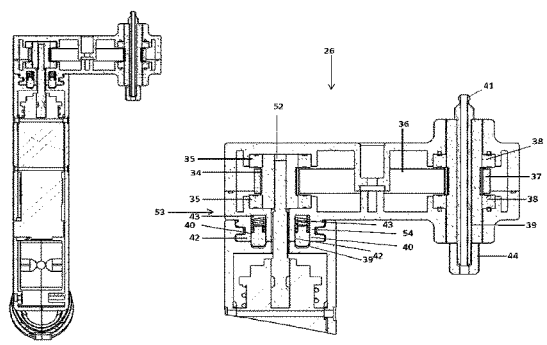
Figure 13

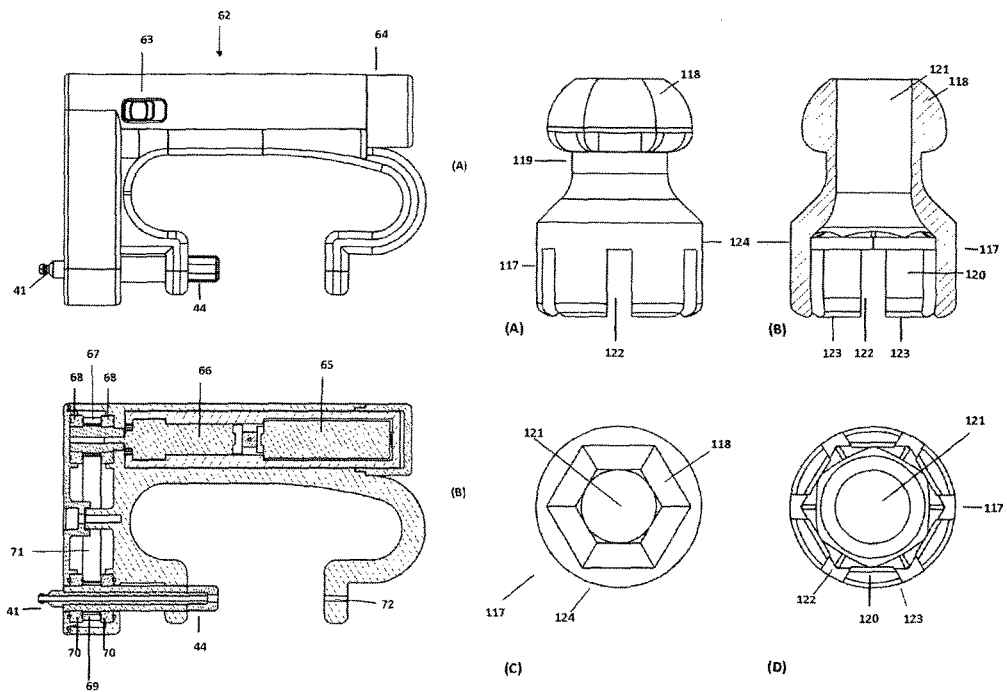
Figure 17
Figure 26
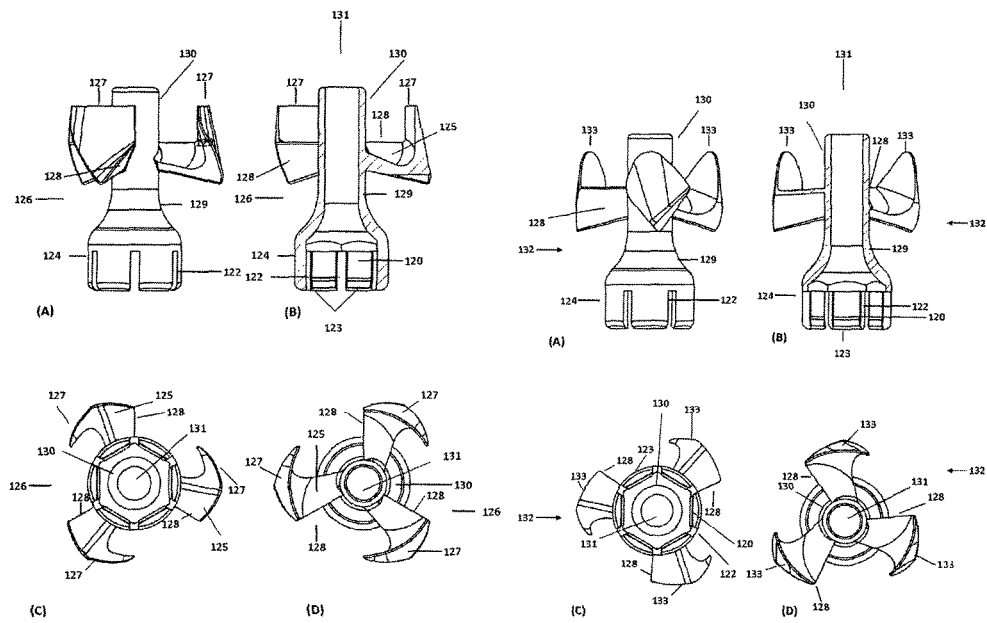
Figure 27
Figure 28

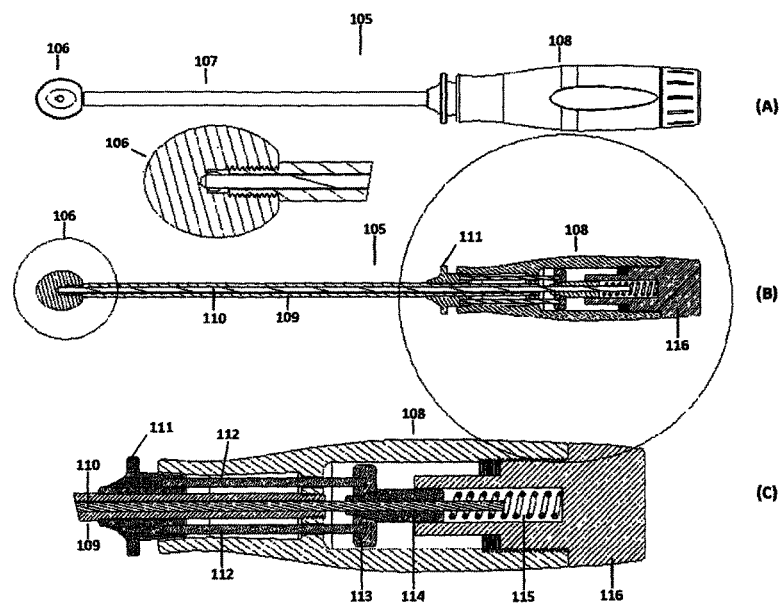
Figure 23
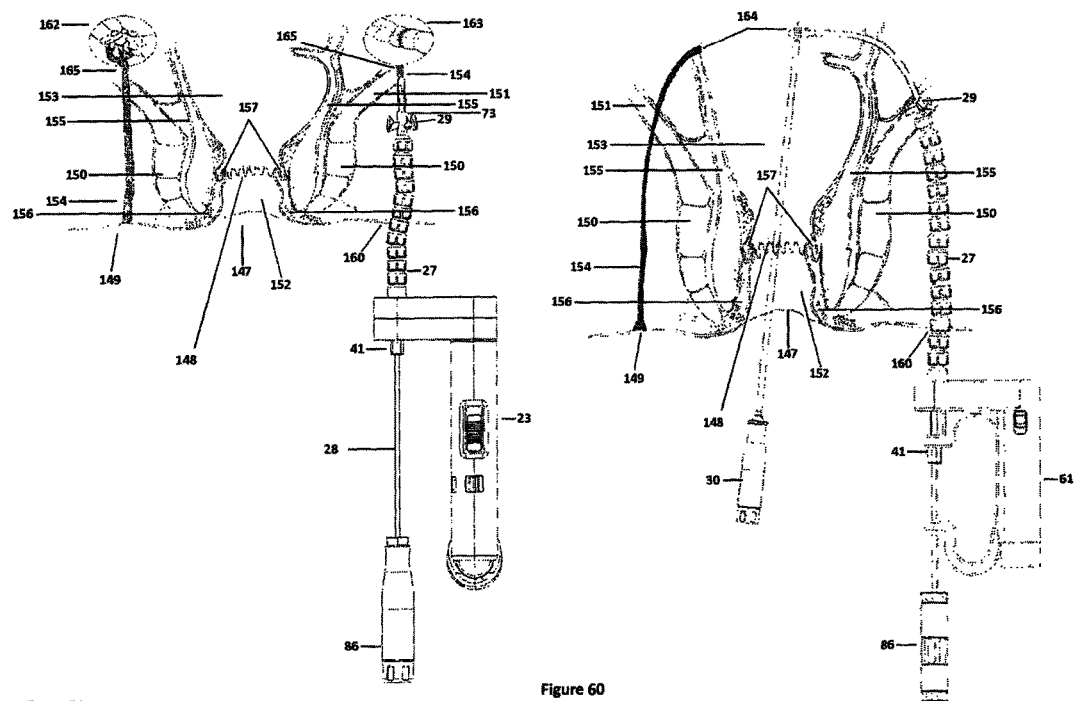
Figure 59
Figure 60

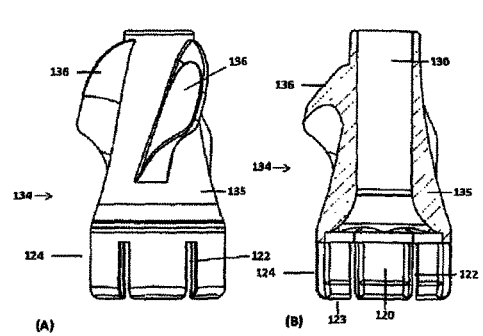
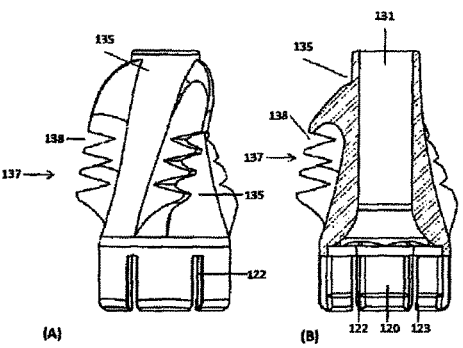
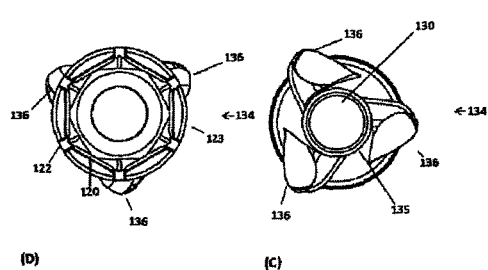
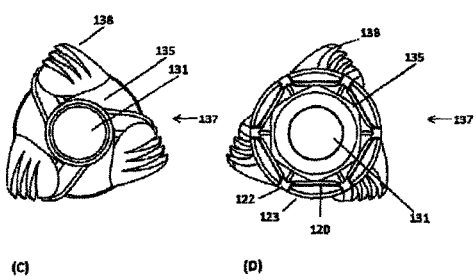
Figure 29
Figure 30
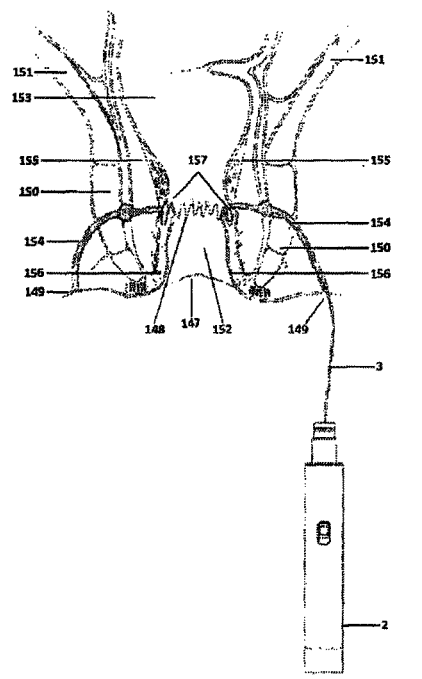
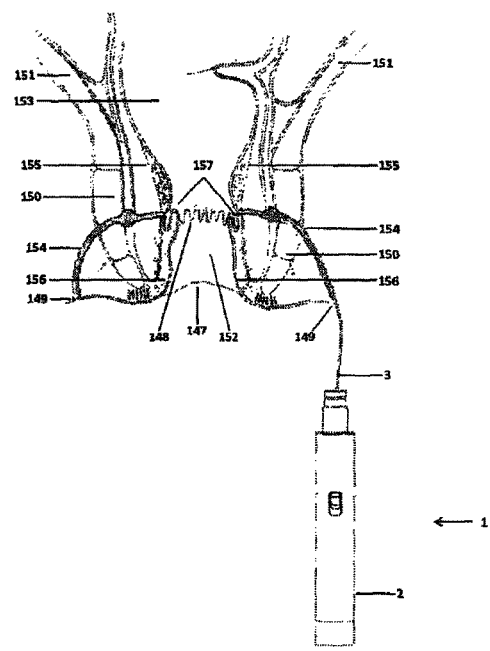
Figure 34
Figure 35

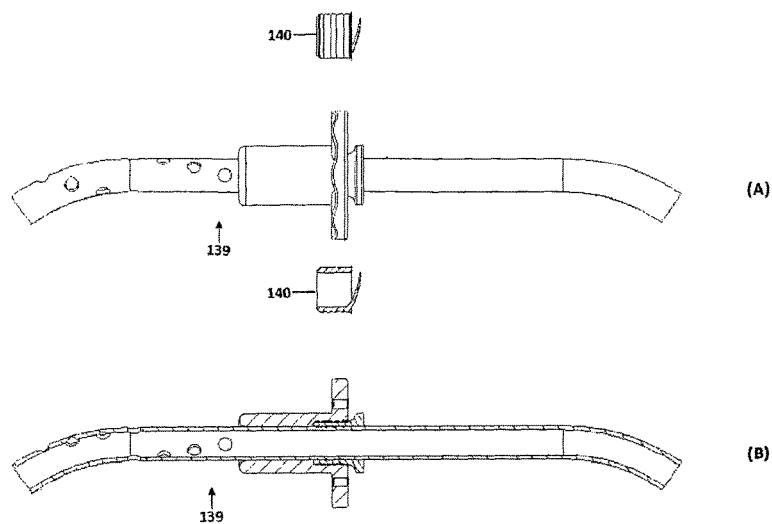
Figure 31
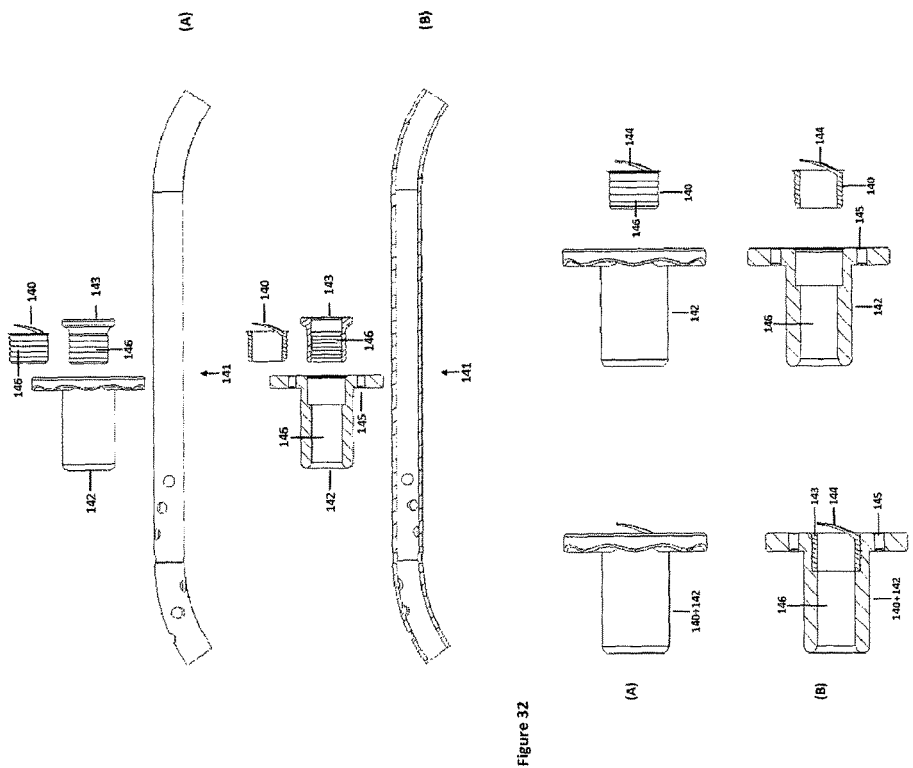
Figure 32
Figure 33

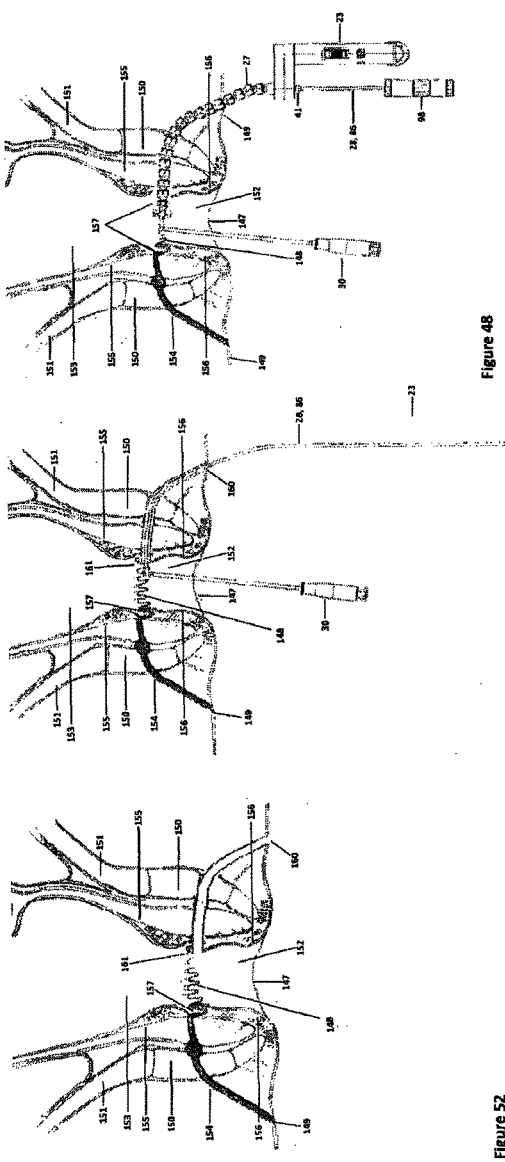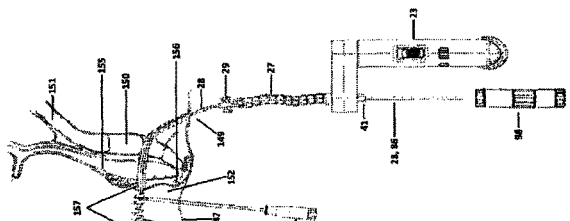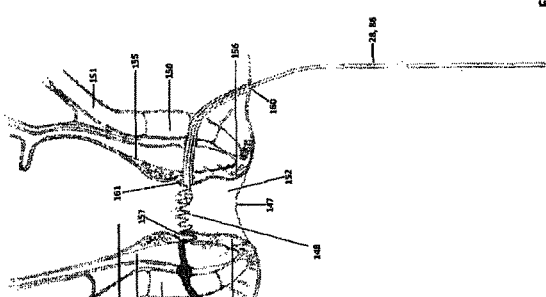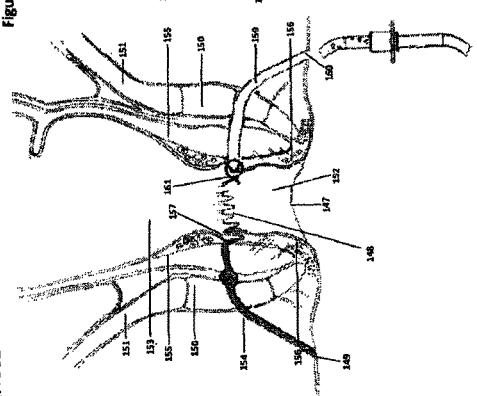
Figure 48
Figure 49
Figure 50
Figure 51
Figure 52
Figure 53

SYSTEM FOR EXCISING ANAL FISTULA TRACES

FIELD OF THE INVENTION

Current invention relates to a method and device for Anorectal Fistulectomy treatment. More specifically, current invention relates to a surgical instrument used by putting the fistula trace in a correct manner and precisely centered in order to remove the unhealthy tissue in a cylindrical shape and a method therefor. The device is primarily designed for treating the anorectal fistula with effective minimally invasive surgery in a short time.

BACKGROUND OF THE INVENTION

Since the anatomic and physiologic structure of the anorectal section carries too specific features, treatment of the fistulas occurring in this area brings with it many difficulties. Taking into account that intersecting external sphincter and—puborectal—muscles will cause anal incontinence during the treatment, it is necessary to maintain the integrity of these muscles to a large extent. Anal fistulas can be examined under two categories, simple (can be treated with fistulotomy) and complex (when the fistulotomy contradicts/counteracts). Basic fistula can be treated easily by fistulotomy and—can be left—for secondary intention. In complex fistulas, set-on application or periodic surgeries are the methods used in order to remove the fistula trace.

This application is not only persistent but also hard for the patient and the treatment concludes with failure due to the high rate of incontinence risk. The treatment principle on fistulas, removing the dead tissues at the fistula trace, moving away the excreting mucous and opening the bloody tissue in order to stimulate the granulation tissue which helps filling the trace.

Although this purpose is achievable with fistulotomy in basic fistulas, fistulotomy cannot be applied in complex fistulas as it will cause anal inefficiency. By gradually cutting the muscle tissue, which forms the sphincter, a method will be applied that will provide healing fibrous tissue.

The cut is executed while the reaction starts with cutting the muscle mass which develops granulation tissue, merging the execrated muscle tissues with fibrous structure and the expectation of filling the fistula trace. While this is not always successful, it causes loss of continence in a certain ratio due to the sphincter dysfunction which fuses with the fibrous tissue.

Hence, there is a need for a device to cure such fistulas.

DESCRIPTION OF THE INVENTION

This invention is capable of overcoming any encountered issue concerning the fistula treatment up until today. It can be easily applied to every anorectal fistula. Especially in complex fistulas, it simplifies a risky operation and provides complete healing in short time.

While the operation done with this instrument preserves the anatomical and physiological structure, it is also in accord with the necessary principles of the fistula treatment. The invention is an instrument which transmits the rotational movement transferred from the electric motor to the cutting edge at its most extreme with the help of a flexible shaft composed of hexahedron units. It takes place on a spiral guide placed on the fistula trace, directed by the guide, in a three dimensional, full and controlled manner. In this manner, it enables the cutting edge to be used with the intended purpose.

Current invention provides a movement providing and transmitting apparatus for providing movement to a movement carrying flexible shaft of a fistulectomy unit as defined by the features of claim 1. Current invention provides also a fistulectomy set as defined by the features of claim 7. Other aspects of the current invention are defined by the features of the appended claims which are incorporated herein.

1) Current invention relates to a system which locates and excises the traces of anal fistula. It consists of the cannulation guide which identifies the fistula trace fully and accurately, and the fistulectomy set which excises the trace on the carrier guide which is placed on the identified fistula trace.

2) According to aspect 1, the cannulation guide system is a mechanical apparatus, the end portion of which is a shaft system including a flexible shaft rotating, vibrating and reciprocating simultaneously and it is also a movement converter with a handle that generates the movement of the shaft.

3) According to aspect 1, the fistulectomy set is an apparatus which consists of fistulectomy and stabilizer systems and a train system which transfers the electromotive induced pivotal movement it contains to the cutting units mounted on the end portion with the aid of a spheroid shaft by carrying on a central carrier guide.

According to aspect 2 is a motion converting apparatus. This apparatus is a mechanical structure which converts the rotational motion from the electromotor (17) it contains to a rotation, vibration and reciprocating motion by the bearing (15), which is mounted on it, rotating on the circular sine curve (21) shaped surface (or cam shaped surface).

5) According to aspect 2 is a flexible shaft system which is characterized together with a flexible shaft which includes a conical spring (7) at the rear which aside from transferring the simultaneous rotation, vibration and reciprocating movement, fixes and controls the tracking part (4).

6) According to Aspect 3 is the mentioned fistulectomy consisting of a medium section (25) containing an electric motor (51), a 180° rotatable shank (24) mounted to the middle section from the rear bottom side and a 360° rotatable front section (26) which is mounted on the axis of the middle section from the front and can be adjusted to left, right, left hip and right hip use, transmitting the rotation movement produced by the motor at the mid-section which works by the energy from the battery at the shank to the flexible motion bearing shaft (27).

7) According to aspect 3 the motion carrier is the flexible shaft characterized by a hinged spiral structure which has the ability to curl in all directions, formed in a predetermined length by adding the spheroid units in succession, moving depending on the guide's orientation on the carrier guide passing through the channel in the center consisting of a spheroid unit (117) which carries the electromotive induced axial rotation from the functional part (41) to the cutting units (29).

8) According to aspect 7 is that each of the mentioned spheroid units are elements each of which consists of a front section (118) formed from six spheroid surfaces, the front sections of which are cut, rear sections flattened and sides symmetrical. These are made up of a rear section (124) consisting of ellipsoid incisions which prevent the removal of the ellipsoid part at the lower ends of the surfaces and six concave surfaces, corresponding to the ellipsoid surfaces at the front section, designed in such a way that one spheroid unit can enter the front section of the other. They also consist of a neck portion (119) in the center which connects the front and the rear section including channels (121) for the carrier guide to pass.

9) According to aspect 3 is the fact that the cutting units are elements which have the structure of the two different cutting edges cutting the tissue they encounter externally and internally, provided with axial rotary movement of the shaft mounted to the tip of the motion carrier flexible shaft (27).

10) According to aspect 9 are cutting units which cut externally; each of these units is an element in two model spheroid units (117) of which include channels (131) for the carrier guides to pass from within which rear portion (124) cutting edges (127, 133) were mounted. It includes a cylindrical portion (130) which is enlarged to adapt to the rear part, and includes a flat-blade (126) cutting edges which cut only the front part or ellipsoid cutting edges (132) from the front and from both sides.

11) The internally cutting units according to aspect 9 are structures which include the second model. They consist of a rear section (124) which has the same structure as the rear section of the spheroid units, of a conical cylinder base (129) resting on this part and narrowing from the rear to the front and a flat blade first model (134) which is longer than the cutting part attached to the concave cylinder portion facing the rotation direction expanding from the front to the rear mounted on the base mentioned and in addition to this model, a second model of the rear section of the cutting edge which has the structure of a saw tooth (137)

12) According to aspect 3 is the carrier guide which is any of the functional flexible guide types that are hard and conventionally flexible.

According to Aspect 12, the hard guide (73) consists of hard steel rods (76) which are secured to the rear portion of the guide blocker apparatus. They pass through the channel which is found in the carrier shaft (27) and determine the direction (74). They are softened rods entering the fistula trace and have stoppers at the tip which are hard at the rear section.

14) According to aspect 12 is the conventional flexible guide. It consists of a spring wire, to the tip of which a stopper (79) was mounted (82) and a rigid cylindrical metal rod (80) mounted on a flexible portion (78) which enters the fistula trace and which consists of a spring wrapped round this wire (81).

15) According to aspect 1 is the functional flexible guide. These are functional guides which act as rails for the motion carrier shafts mounted on the stretching spring and the guide stabilizer (98) ending with a tube mounted on the rigid wire, the rear of which is covered with a moving tube (94) the middle of which is on the rigid wire (95) bearing flexible (97) or a spring flexible (87) the front section of which enters the trace mounted (154) with a stabilizer (105) and a guide stopper, the tip of which enters the rectum by placing it in the fistula trace.

16) According to aspect 3 are stabilizer units. They include the guide tip clutch apparatus, a rigid and conventional guide securing the handle and a functional flexible guide stabilizer and a stretching shaft.

17) According to aspect 16 is the guide tip clutch apparatus. This is the apparatus which compresses and stabilizes the tip portion to the hollow stabilizer portion (106) with the aid of the steel wire in the tubular mid-section (107) by moving the tip of the functional guide which goes through the fistula trace into the rectum by moving the spring system at the shaft (108) with the pusher (111) in the front section of the shaft.

18) According to aspect 16 is the rigid and conventional guide stabilizer which provides the forward movement of the rigid and conventional guides by loosening the collet (83) with the spring (84) placed around the pens and stabilizing the rigid rear sections by tightening the back cover (85) with the aid of the collet.

19) According to aspect 16 is the functional flexible guide stabilizing and stretching shaft. It is the apparatus which removes the moving section (88) and the stable rear section of the functional guide by moving the front and rear clamp retainers (104 a, b) when the bearing series (93) are compressed and stabilized and the free spring (93) at the front section of the flexible part of the functional guide (86) is stabilized, the rear collet (99) which covers the rear screw (100) is stabilized by the stable section (89) at the rear, the front collet (102) covered by the front screw (103) which stabilizes the moving tube at the mid-section of the functional guide (86).

20) According to aspect 3 is the drain system placed in the fistula trace. This is the drainage system in which the cylindrical (140) cover is placed instead of the drain stabilizer (143) when the drain is pulled including the drain stabilizer (146) which includes the drain stabilizer at the front section stabilizing the drain (141) which passes through the skin, and which is placed in the channel (154) formed after fistulectomy.

1) Cannulation Guide System: Rotation, vibration and reciprocation work together in the same apparatus in a single system in the set.

2) Motion provider and relay apparatus: The set is structured in such a way that the handle can be used reversed with a 180° front part (90°, 180°, 270°, 360°) which can turn in four directions according to the adaptive use of the right hand, left hand and right and left hip.

3) Hard Guide: The guide's front section which enters the trace is softened and elasticized.

4) Functional Guides: A fistula trace stabilizer system was formed by a pipe system which presses the bearing sequence or the free spring in the front of the back side of which a free spring or bearing sequence is attached onto the hard rod at the back, which is wrapped on a steel spring at the end portion.

5) Fixing guide and clamping handle: The functional driver and receiver consists of a complicated structure with the receiving spring system on the set.

6) Flexible motion bearing shaft: A shaft which moves in 6 directions simultaneously (60°) has been developed on the set.

7) Functional blades formed by tissue types have been developed on the set.

DESCRIPTION OF DRAWINGS

FIG. 13) Connection of the mid-section and the front section of the diagram which shows the details of the shapes of the places of the motion provider and transmitter apparatus FIG. 14) Functional state of the fistulectomy set (shaft is at the bottom): A) System works from right position, B) System works from left position, C) System works from upper position FIG. 15. Functional state of the fistulectomy set (handle inverted): A) System works from right position, B) System works from left position, C) System works from below position FIG. 16) Practical fistulectomy set: A) Installed, B) Uninstalled, overall view FIG. 17) Body portion of the practical fistulectomy set, motion provider and transmitter: A) Overall view, B) Section view FIG. 18) Hard guide: A) Uninstalled and installed overall view, B) Uninstalled and installed section view FIG. 19A) Conventional guide: A) Uninstalled and installed overall view, B) Uninstalled and installed section view FIG. 19B) Rigid and conventional guide handle: A) Overall view, B) Sectional view, C) Schematic section of the installed guide FIG. 20) Functional guides: A) Schematic section and detailed views of the spring-wound functional guide, B) Schematic section and detailed views of the bearing functional guide, C) Section view of the functional guide installed to the fixing and stretching spring FIG. 21) Functional guide securing and stretching shaft: A) Schematic, B) Section schemes FIG. 22) Securing and stretching shaft of the functional guide: A) Schematic and section views and details of the secured guide, B) Schematic and section views and details of the secured guide in a securing and stretching state. In the detailed view, the separation between the moving mid-section and the secured rear section can clearly be seen following the securing and stretching process.

FIG. 23) Guide handle holding and securing apparatus: A) Schematic, B) Section, C) Detailed views of the sections of the shaft part FIG. 24) Functional positions view of the movement carrier flexible shaft FIG. 25) Section and detailed views of the movement carrier flexible shaft FIG. 26) Hexahedron spheroid parts of the movement carrier flexible shaft: A) Schematic, B) Section, C) Top, D) Bottom views FIG. 27) Externally cutting flat blades: A) Schematic, B) Section, C) Top, D) Bottom views FIG. 28) Externally cutting conical mouth blades: A) Schematic, B) Section, C) Top, D) Bottom views FIG. 29) Internally cutting flat blades: A) Schematic, B) Section, C) Top, D) Bottom views FIG. 30) Internally cutting saw tooth blades: A) Schematic, B) Section, C) Top, D) Bottom views FIG. 31) Installed fistula drainage system: A) Schematic, B) Section figure FIG. 32) Uninstalled fistula drainage system: A) Schematic, B) Section figure FIG. 33) Drain stabilizer and stabilizer closing parts: A) Schematic, B) Section figure Stages of fistula treatment are pictured from FIG. 34 to FIG. 55.

FIG. 59) shows the fistulectomy process in a pelvic inflammatory fistula schematically.

FIG. 60) shows the fistulectomy scheme in a practical fistulectomy and extrasphincteric fistula.

Figure 1:
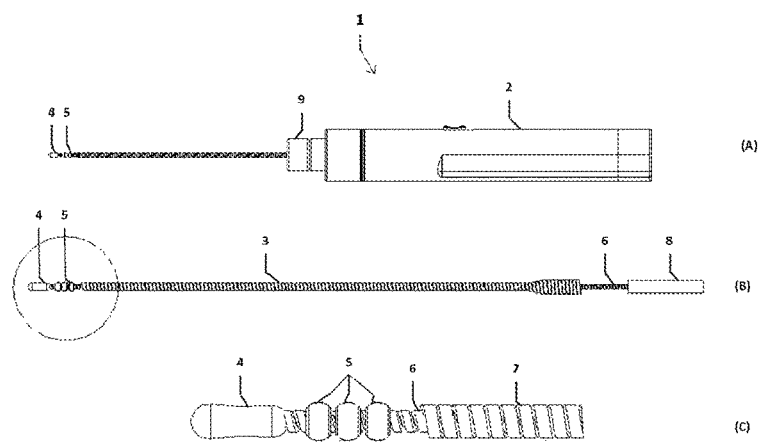
FIG. 1) Cannulation guide apparatus: A) Overview of the apparatus, B) Overview of the flexible guide system, C) Schematic detail view of the end portion of the flexible guide system FIG. 2) Cannulation guide parts: A) Sectional view of the apparatus, B) Detailed view of the section of the motion converting section FIG. 3) Sectional view of the parts composing the cannulation guide apparatus: A) Sectional view of the motion provider and converter shaft section, B) Section view of the flexible guide system, C) Section view of the flexible guide, D) Section view of the conical spring winding the flexible guide FIG. 4) Section view from above of the curve-shaped structure of the cannulation guide apparatus which provides vibration and reciprocating on the sinusoidal curve FIG. 5) Fistula trace detection of the cannulation guide apparatus (section on the left), on the right, the schematic image which demonstrates that false paths may form with a rigid citric FIG. 6) Fistulectomy system: A) Fistulectomy system of the installed figure, B) Fistulectomy system of the uninstalled figure FIG. 7) Motion provider and transmitter apparatus: A) Overall view, B) Section view FIG. 8) Motion provider and transmitter apparatus: A) Uninstalled overall view, B) Uninstalled section view FIG. 9) Front section of the motion provider and transmitter apparatus: A) Overall view, B) Detailed view FIG. 10) Handle of the motion provider and transmitter which includes the battery: A) Overall view, B) Section view FIG. 11) Sectional and the detailed view of the mid-section of the motion provider and transmitter apparatus which includes the motor FIG. 12) Detailed view of the connection section of the transverse of the shaft and the mid-section of the motion provider and transmitter apparatus: A) Installed section, B) Schematic section of the separation process which turns the shaft 180°
Figure 2:
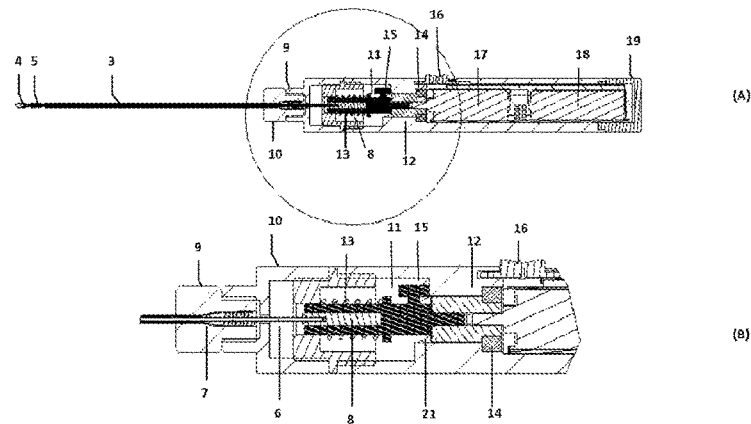
Figure 3:
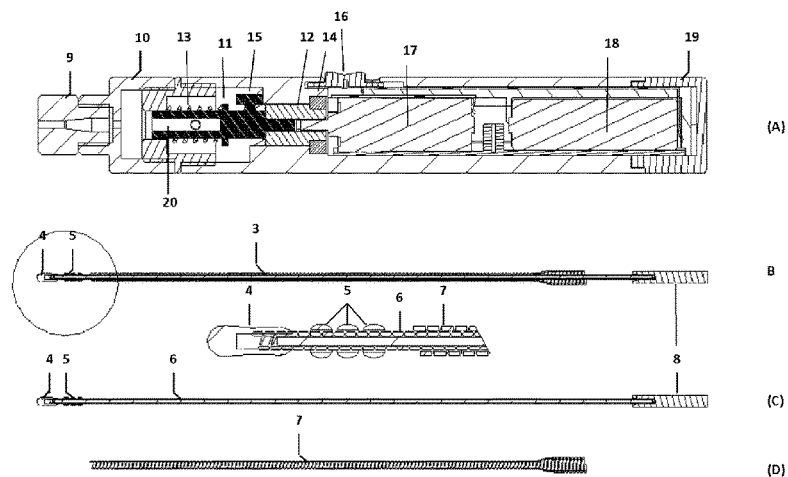
Figure 5:
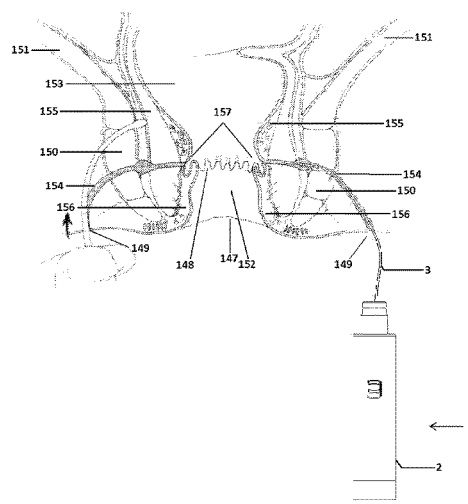
Figure 6:
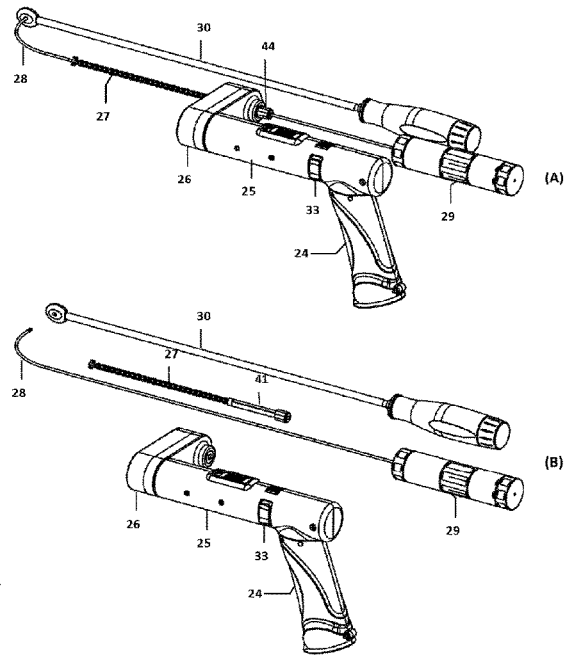
Figure 7:
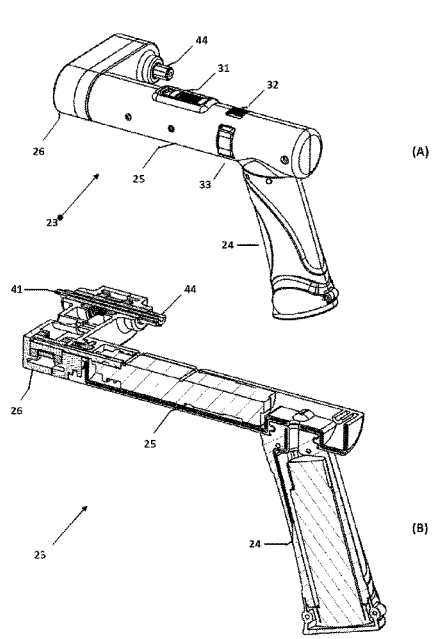
Figure 8:
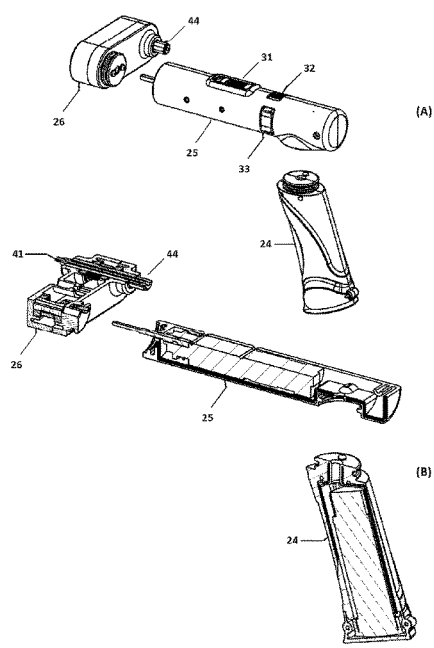

DETAILED DESCRIPTION OF PREFERRED EMBODIMENTS OF CURRENT INVENTION FISTULECTOMY SET

I. Main Elements
A) Cannulation Guide Apparatus (1)
B) Carrier Guides (72, 73, 86)
C) Flexible Movement Carrier Shaft (27)
D) Cutting Edges ([29], 126, 132, 134, 137)
II. Support Elements
E) Movement and Transmission Apparatus (25)
D) Holding and Hooking Parts
G) Drain system corporated into fistula trace
Description of the Elements which Form the Fistulectomy Set
I. Main Elements
A) Cannulation Guide Apparatus;

Determining the fistula traces (149) accurately is an indispensable process for the treatment. The trace is formed by soft tissue, a muscle layer, granulated tissue and fibrous sections. Cannulation Guide is a complex apparatus which enables complex movement, developed for focusing on fistula traces which course through the aforementioned structures without diverting it.

It is an apparatus which transmits the axial movement with the aid of the flexible shaft to the raindrop shaped edge as a complex movement (turning, forward, backward, vibration). The holding stick (2) transmits the centralized rotation movement inside of its electromotive force (17) which is secured to the bearing (14), to the cylindrical structure (12) which transmits to the moving part (11). Vibration and reciprocation is obtained with a rotary motion on the surface of the bearing (15) which is mounted on the moving part on small protrusions (provides vibration) (22) found on the whirling circular sinusoidal surface (21) which is transmitted to the moving part. (11) The reciprocation (can be) restricted by loosing/tightening the spring on the moving part. With the aid of the quadrilateral (8) part which can be found on the back section of the flexible guide that is mounted on the front channel (20) of the moving part, these three acts of movement (rotation, reciprocation, vibration) can reach the drop shaped structure (4). In order to prevent the friction between the conical spring (7) mounted on the flexible guide and the drop shaped (4) end, bearings (5) have been put in place. The conical part of the spring (7) which wraps the exterior of the flexible guides can be secured to the frontal part (10) with screws (9) so that the flexible guidance system (3) can be stabilized. The energy of the system can be provided by electricity or battery (18). It is possible to provide energy with the battery (18) which is installed under the lid behind of the switch that is implemented behind the flexible guidance system (3). Powering up/down can be done with the button (16) on the switch. If desired, by installing a camera on the drop shaped end of the cannulation guidance system's flexible guide, the process of finding the fistula trace can be supported with visuals.

B) Carrier Guides (73, 77, 86);

Carrier guides (73, 77, 86) are the carriers which provide movement depending on the direction of the flexible shifting carrier shaft (27), installed on the fistula trace.

They come in two different structures

1. Hard Guides (73)
2. Functional Flexible Guides: a) Conventional Flexible Guides (77), b) Functional Flexible Guides (78)

Hard Guides (73)

Having a stopper (79) on its edge, these are cylindrical rods; the soft, pliable (74) end of the rod enters into the fistula trace and the other end is rigid (80). In view of the ease of utilization, the rigid parts of the back sides can be secured to the securing rod (76), to the tightening pliers (83) on the front with the aid of a stretching nut (85).

Flexible Guides a) Conventional Flexible Guides (77)

It consist of a wire (82) wrapped by a spring (81) and has a stopper (79) with a rigid cylindrical metal rod (80) which is mounted on the frontal flexible part (78) for easy entrance to the fistula trace. Just like in the hard/solid guide, to provide easy utilization, the rigid part can be mounted to the guide securing rod (76) and the tightening pliers (83).

b) Functional Flexible Guides (78)

It consists of a flexible spring wire (91), wrapped with spring (92) and a stopper (90) on the end. This main assembly wrapped by a spring (93a) or by the bearings (93b) lined in a row which enters into the fistula trace with its frontal flexible part, also consists of a solid cylindrical rod wrapped with steel spring (91), is a carrier (89) element which is secured by the cylindrical rod with a moving cylindrical rod.

In order to secure it to the fistula trace and to take its form, functional flexible guide (86), the spring on the flexible part and the bearings (93, a, b) are to be secured to the functional guide securing and tightening rod (98).

The functional guide's middle (88) and back portion are to be transmitted until the end (89) of the functional securing and tightening rod (98) through the conduit in the center.

The last part of the guide (89) secured to the pliers in the middle (102), middle portion secured to the frontal pliers (99), front (100) and rear (103) pliers fastened with the nuts in order to fix the guide. By rotating the nut (101) in the middle part, the middle and rear portion of the functional guide can be set aside, in order for it to take the shape of the fistula trace so that the fistula treatment can be done in the correct position, and tighten the spring (87) in the front portion. If desired, the springs of the flexible guide can be coated with plastic in order to reinforce its durability and lubricity.

C) Flexible Movement Carrier Shaft (27);

It is an articulated spiral assembly consisting of consecutive hexahedron units (117). The cutting edge is mounted to the front part and to the frontal part of the apparatus which provides movement and transmission. The cutting edge ([29], 126, 132, 134, 137) is mounted on the front portion, the front part of the movement transmitter (23) is mounted on the rear side of the apparatus which provides movement and transmission, the hexahedron part that is meant to be mounted in the middle of the distal sprocket (38) is to be mounted as if it is a part of it, which the rear side is rectangular and the front part is spheroid (117). Depending on the orientation of the guide, a flexible carrier shaft transmits the movement to the furthermost cutting edge (29).

Hexahedron Spheroid Units

These are the units which are assembled into the flexible shaft (27) by being mounted on each other to form an articulated spiral. They consist of three parts. The front part (118) is cut and consists of six symmetrical oblate spheroids, the rear part (124) is designed to connect to the other spheroid part, and the middle part, neck portion (119) provides the connection between two parts. Six concave surfaces (120) which oppose to the rear and front surfaces. Six channels (122) corresponding to these surfaces and side protrusions. The edges of the surfaces contain ellipsoid protrusions (123) which prevent the spheroid parts from getting out. The channel is a passage which is present to provide mobility for the transmission guides between the units. (121)

D) Incisory Units;

These are mounted on the edge of the flexible shaft (27) to excise the tissue encountered with axial rotation.

There are two models present: 1. Exterior Incisory Units (127, 132); 2. Interior Incisory Units (134, 137)

Exterior Incisory Units

These consist of three sections. The rear side of the spheroid units (117), the rear side (124) of the hexahedron, which has a connection to the frontal part that enters the front section of the spheroid units (118), has the same structure as the rear of the hexahedron units.

The channel (131) where the blades (127, 133) are installed, is an extensible cylindrical part for the carrier guides to pass through, which accordingly is on the rear.

Cutting edges are installed on the cylindrical mouth (127, 133). The upper parts of the angled graspers (125) which mount the cutters to the chassis has the structure of a cutting edge which is capable of excising the tissue at full length and which is excised in the shape of the cylindrical pipe, throwing them in the direction of the cutting edges (128).

The exterior incisory units have two different structures; one of them has only one straight blade which excises only the front part, the other one is an ellipsoid and frontal-sideward excision.

Externally cutting blades are composed of two structures; the flat blade (127) which cuts only the front section and the ellipsoid blade (133) which cuts from the front and from both sides.

Internally Cutting Units:

Its rear sections have the same structure as the rear sections of the spheroid units (124). A conical cylindrical base (129) resting on the rear section and narrowing from the rear to the front and a flat blade first model (134) which is longer than the cutting part attached to the concave cylinder portion facing the rotation direction expanding from the front to the rear mounted on the base mentioned and in addition to this model, a second model; the rear section of the cutting edge which has the structure of a saw tooth (137)

II. Support Items

Figures 9, 14, 15, 16:
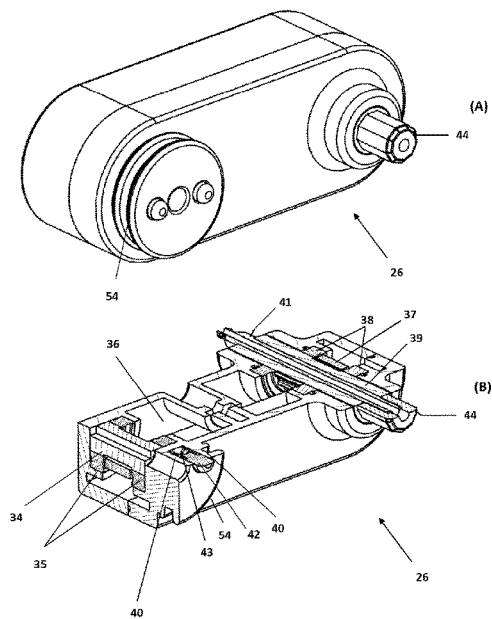
Figure 18:
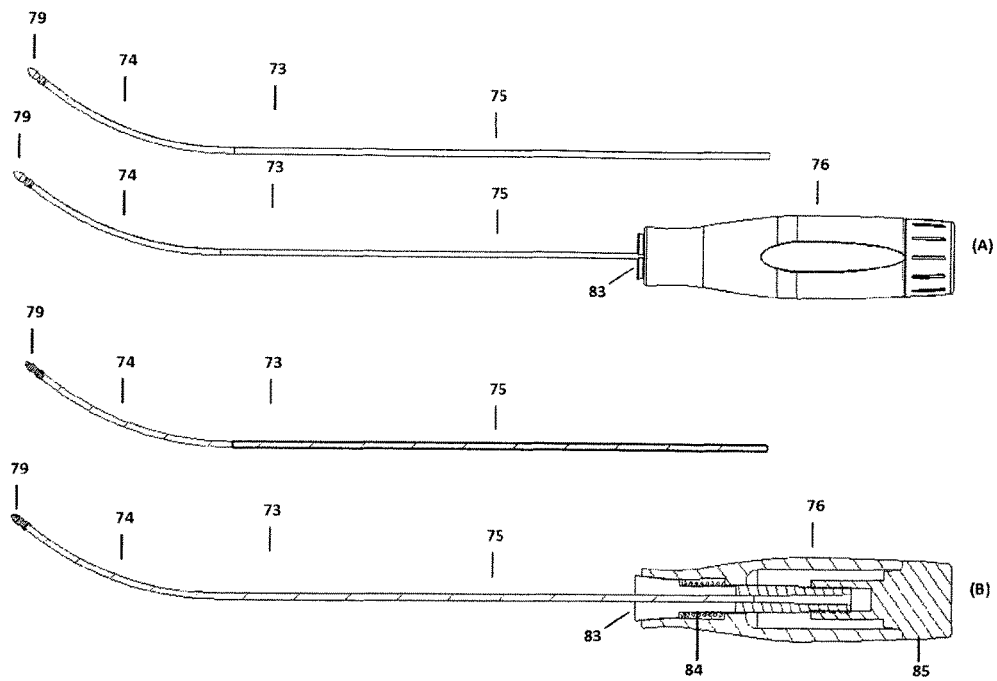
Figure 19A:
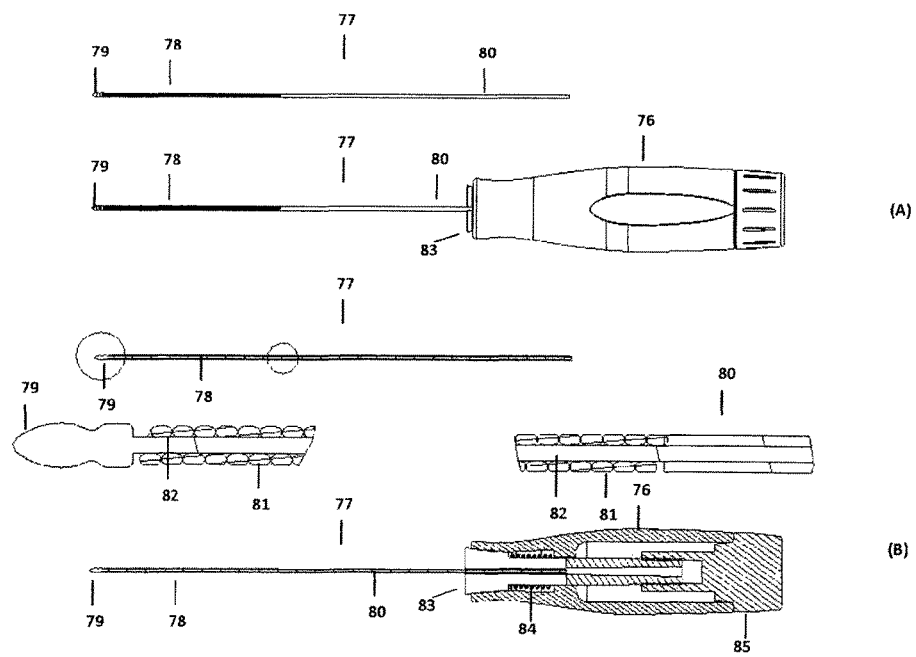
Figure 19B:
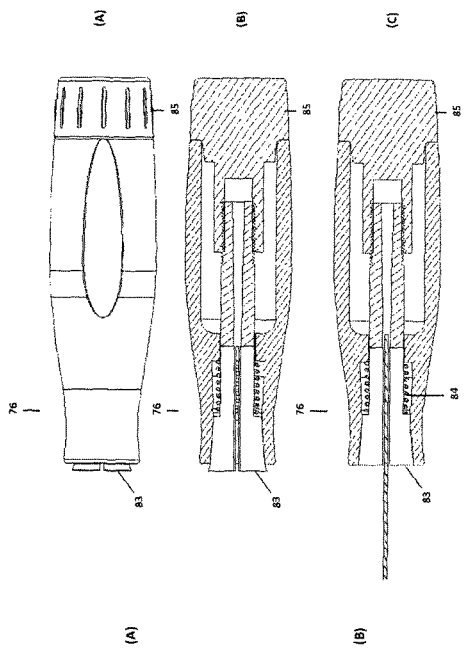
Figure 20:
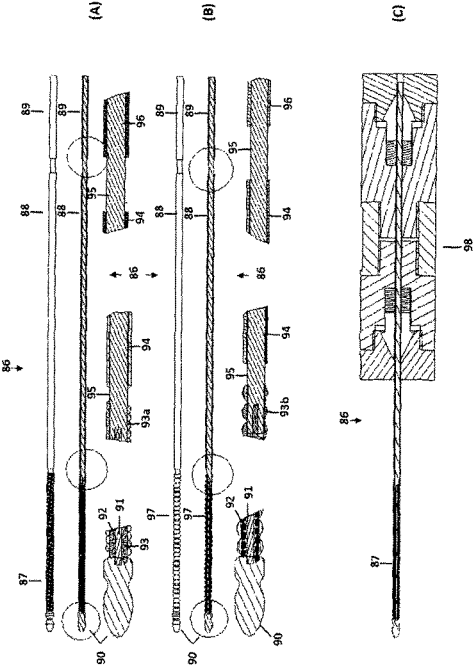
Figure 21:
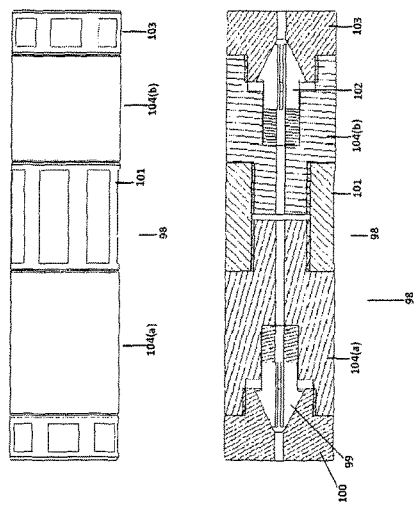
Figure 22:
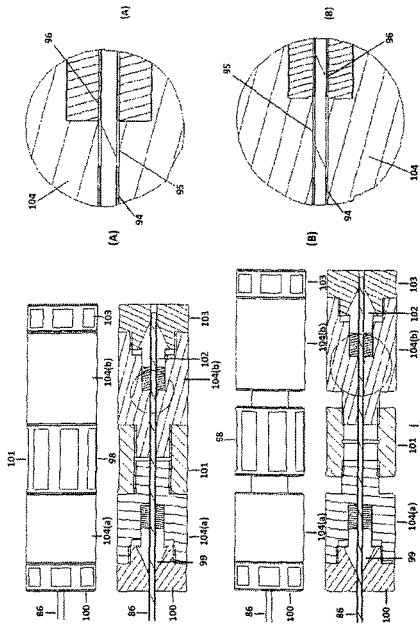
Figure 24:
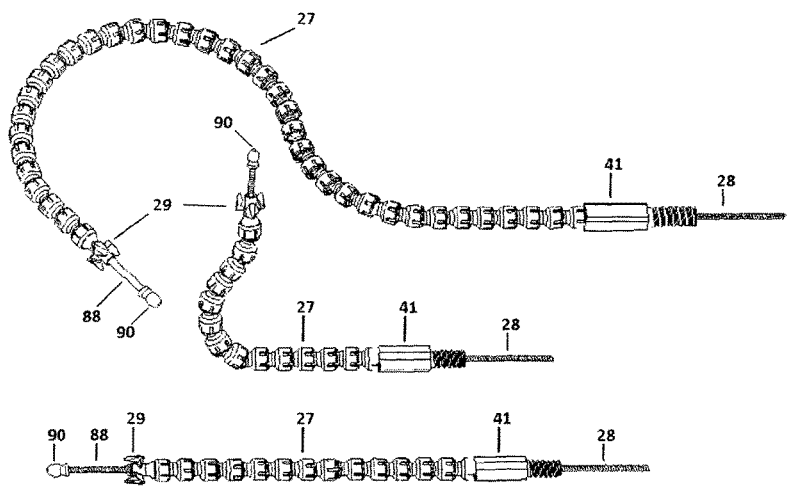
Figure 25:
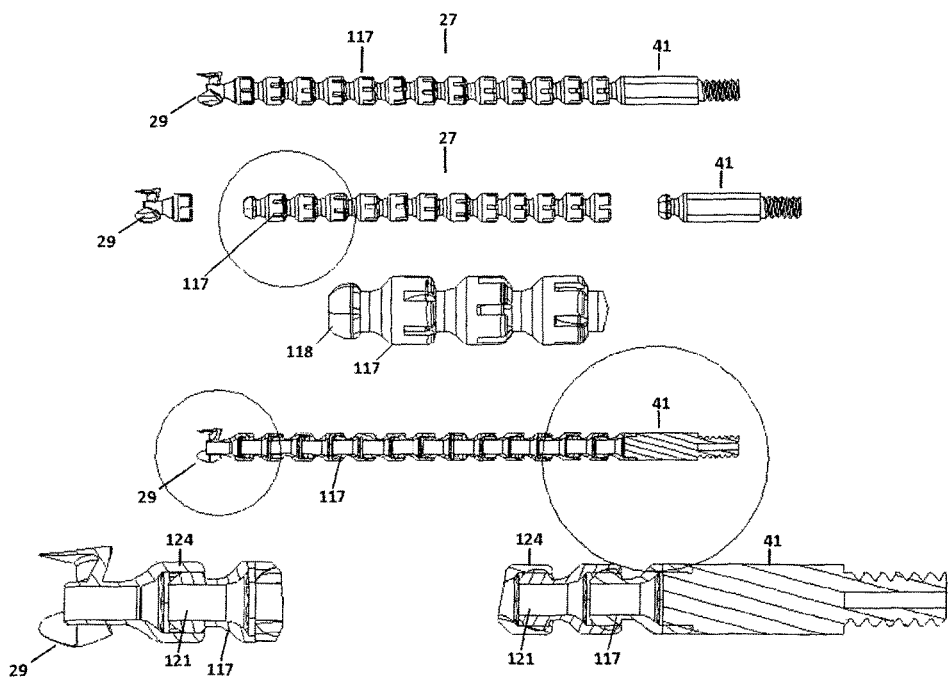

E) The Apparatus that Detects and Transfers Movement (23);

This is a system which transfers the rotation movement supplied by the electric motor in the handle to the movement carrier flexible shaft. It has two models: 1) Apparatus providing and transferring functional movement; 2) Apparatus providing and transferring practical movement APPARATUS PROVIDING AND TRANSFERRING FUNCTIONAL MOVEMENT It consists of a handle and a mid-section (25) containing an electric motor (51), of a 180° rotatable shank (24) mounted to the middle section from the rear bottom side and a 360° rotatable front section (26) which is mounted at the axis of the middle section from the front side. These features enable it to be adjusted to left, right, left hip and right hip use which transmits the rotation movement at an inverted or flat position (FIGS. 14 and 15).

It consists of three parts;

a. If a battery is used as an energy source, the handle in which the battery (49) is located.

b. The mid-section (25) which transfers the rotation movement produced by the electric motor in which the handle is mounted to the movement transferring rotatable front section (26)

c. The rotatable front section (26) which transfers the rotational movement, which is transferred from the electric motor (51) to the proximal gear (35), to the movement bearing flexible shaft (27) mounted on the distal gear (38) with the aid of a belt (36)

Functional Explanation

The energy provided by the battery (49) placed in the handle with the help of the removable cover (45) reaches the electric motor (51) through the cable passing through the channel at the top (48). Axial rotational movement provided by this energy is transferred to the proximal gear (34) secured with bearings (35) at the front section (26) with the help of the movement transmitting shaft (52) secured at the tip of the motor. It is transferred to the gear (37) secured on the distal shaft with the bearings (38) with the help of the generator belt (36). The mid-section of the distal gear includes a channel (39) mounted at the rear section of the distal gear in which the functional part (41) can be placed transferring the rotational movement by the flexible shaft (27).

It is placed in this channel and mounted to the shaft from the rear section with a screw (44). The rotational movement which reaches the distal gear reaches the flexible shaft (27) mounted to the functional part (41), hence to the cutting edge (29)

Carrier guides when fistulectomy is carried out; the blade is passed from the centers of the movement transferring the flexible shaft and the functional part, and their rear ends are mounted to the guide holding and securing handle.

Turning of the movement providing and transferring apparatus in the opposite direction; It is generated by the pin (59) which is on the spring (60) entering the other gap (across 180°) in the central section (58) upon turning the handle, with the stretching and tightening of the spring, is placed in the channel at the top section of the handle. The fixation of the handle and the shaft is determined by the interweaving of the cylinder (56) at the mid-section, the center of which corresponds to the circular projection and the mid-channel cylindrical structure (46) on the handle.

The circular motion of the movement slider front portion of the movement provider and transmitter apparatus in the mid-section is provided by the rotation of the shaft. It is provided by the rotation of the front section by securing the mid-section corresponding to the spheroid slots (39) which are on the pins (42) located in the structure (43) located in the channels (40) within the cylindrical structure (54) at the junction of the middle of the mid-channel cylindrical structure (54) which are at the central portion of the front section (26) and middle section (25), with the stretching and loosening of the pin (42) from the spherical housing (39) and entering another slot.

The securing of the shaft and the front section is provided by the interweaving of the mid-channel cylindrical structure (54) at the connection point of the front section (26) with the cylindrical structure (53) at the mid-section, the middle of which corresponds to the circular projection. The rotation angle can be set as desired, determining the number of channels as required.

Practical Movement Provider and Transmitter Apparatus (62)

It is a compact system without moving parts. It consists of a shaft, including the battery, with installed motor (66) with the help of the L-shaped back cover (64), bearings with which the rotational movement of the motor is transferred, installed proximal gear (67) and a movement transmitter including installed distal gear (69) with distal bearings (70) the movement of which is transferred with the help of a toothed belt (71). It includes the functional part (41) secured to the shaft with a back screwed guide (44) located in the channel in the middle of the distal edge. The guides passing from the center of the functional part (41) exit by passage through the channel (72) located at the bottom part of the shaft.

Functional Explanation:

The axial rotational movement produced by the motor (66) with the energy supplied by the battery (65) is transferred to the proximal gear (67) with the aid of the motor shaft. It is transmitted to the distal gear (69) which the functional transmitter installed in the moving flexible shaft (27) with the help of the belt between the gears (71). This way, the flexible movement transmitter shaft (27) transmits the movement to the cutting edge at its tip (29).

F) Holding and Securing Parts of the Carrier Guides;

1) Guide tip clutch apparatus (105)
2) Rigid and conventional guide securing handle (76)
3) Functional flexible guides securing stretching shaft (98)

1. Guide Tip Clutch Apparatus (105)

This is the part which grasps the tip of the guides in the rectum and anal channel and prevents it from moving. It supports the guide during the fistulectomy process.

a. Tip (106)
b. Mid-section (107)
c. Part which enables the movement of the shaft (111, 112, 113, 114)
d. Shaft (108)

Tip: ellipsoid shaped, guide in the middle. It contains a hole into which the tip enters.

Mid-section: It is the section between the tip and the shaft. It is composed of an outer tubular part (109), securing the handle and the tip and a shaft securing the guide shaft (110) which passes through the tube and secures it.

Part of the shaft providing movement: This is the quaternary structure which provides the reciprocating movement of the shaft.

It consists of a part repelling the spring (114) which secures the shaft in the handle, a cylindrical cone (111) part which passes through the mid-section, rods (112) installed to this part and a horizontal part (113) to which the shafts transmitting the movement of the rod (114), are secured.

Handle part: This is the part terminated by the back cover which includes the spring including the elements providing the shaft movement (115).

2. Rigid and Conventional Guide Securing Handle

This is the part which secures (85) through screwing the back cover (85) secured by the clamp (83) in the hard rear section of the rigid and conventional guide securing handle. The spring (84) disposed around the collet provides forward movement of the loosened clamp.

3. Functional Guide Securing and Stretching Spring

This is the element which tightens the bearing series (93b) and the spring (93a) on the front section by securing the rear section (89) and the mid-section (88) of the functional flexible guide (86). It tightens these clamps with front and rear stamps (99, 102) which tighten the mid- and rear sections of the guide (86). Front and rear screws (100, 103), front and rear parts to which the stamps are secured (104a, 104b). It is composed of cylindrical screws (101) which reciprocate them by securing these parts.

G) Drain System Placed in the Fistula Trace;

It enables the cylindrical cavity to be drained after a fistulectomy (139). It consists of four parts:

1. Entering into the hollow cylindrical tube and in turn entering the tissue

2. The suberose structure fixed to the skin it passes through the cylindrical tube located in the fictula outer mouth in the gluteal region (142)

3. Guide (146) cylindrical structure (143) which secures the cylindrical tube located in the front section and passing through the suberose structure.

4. Covered cylindrical structure (140) which conducts the drainage until the cavity inserted in place of the drain securing part (143) after the cylindrical tube is removed.

The Conduct of the Fistulectomy Process:

Anorectal fistulas are a curved channel (154) terminated with an inner mouth (157) opening up to the dentate line in the anal channel (152) by colliding inwardly and passing through the external muscle, the internal muscle and the anal mucosa (156) and an outer mouth (149) in the gluteal skin. It can be at m. Lavator ani (151) by changing the fistula channel inner mouth. It may be referred to as a simple versus complicated, high versus low fistula depending on its distance to the entrance of the anus (147)

The fistulectomy operation is the accurate detection of the fistula trace and its excision.

Figure 36:
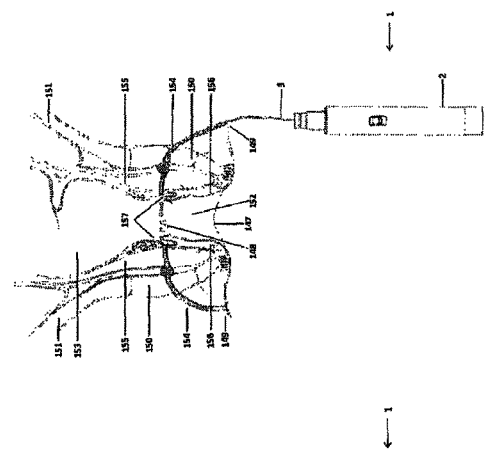
Figure 37:
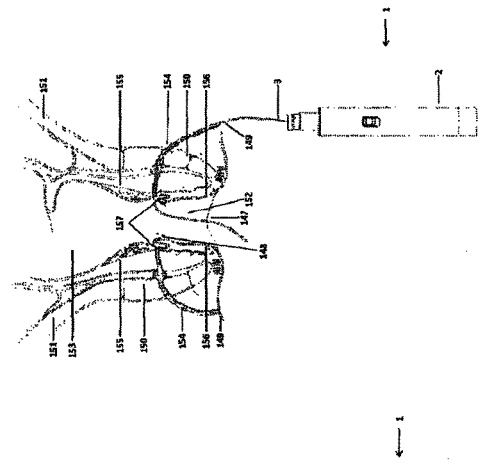
Figure 38:
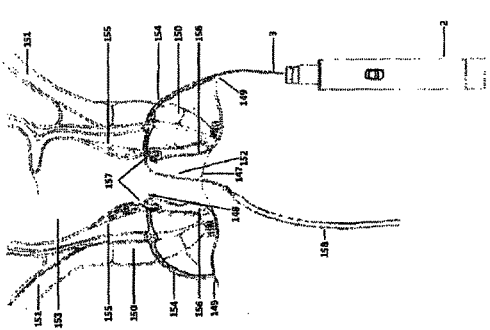

Cannulation the guide is used to detect the trace. This process is; the tip of the cannulation guide (1) of the flexible guide system (3) is inserted into the beads (5) and the raindrop-shaped tip (4) is inserted into the outer mouth (149) (FIG. 34, 35). When continuously pushed, the tip is removed from the inner mouth (157) and reaches the anal channel (152) (FIG. 36). The flexible shaft in the anal channel is caught and removed (FIG. 37).

Figure 39:
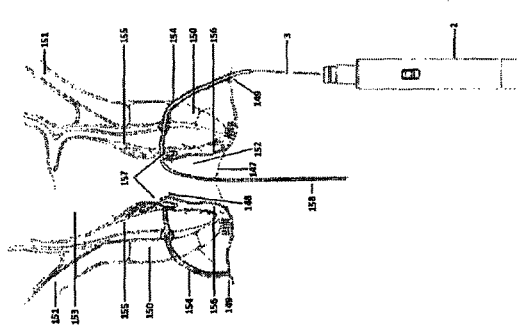
Figure 40:
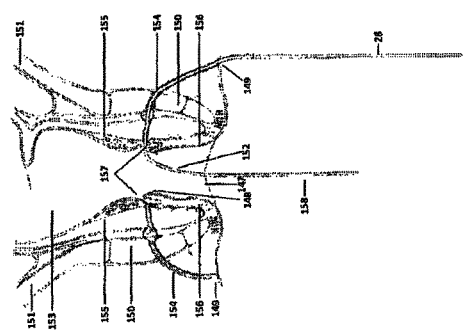
Figure 41:
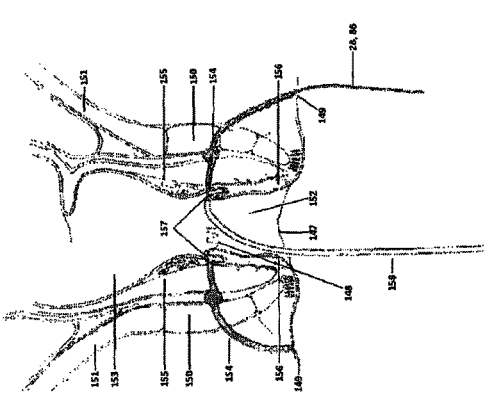
Figure 42:
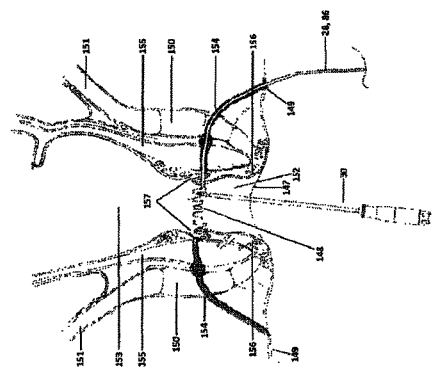
Figure 43:
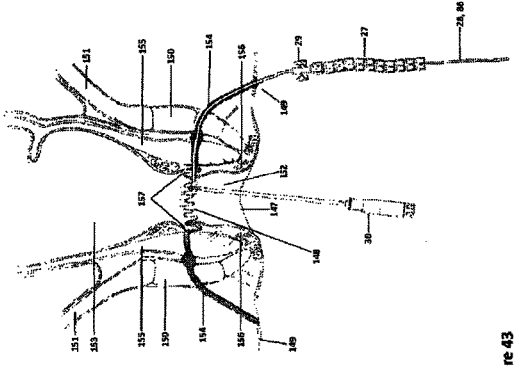

At this point, the fistula trace is removed from the outer mouth and inserted into the trace by pulling the cannulation guide back in order for the functional guide to be inserted into the fistula trace easily (FIG. 39). The tip of the functional guide (28) is installed into the tip of the catheter removed from the outer mouth and it is delivered to the anal channel by slowly withdrawing the catheter installed to the flexible shaft (FIG. 41). Here, the tip of the functional guide is held and secured by the holding and securing apparatus (30) (FIG. 42). The movement carrier guide system is placed on the guide which in turn is placed in the fistula trace (FIG. 43).

Figure 44:
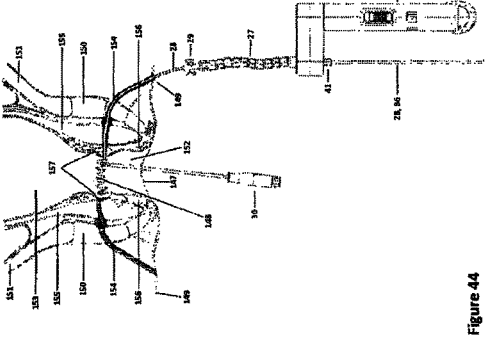
Figure 45:
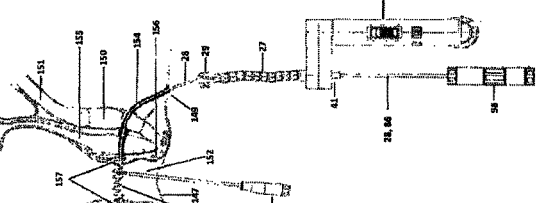
Figure 46:
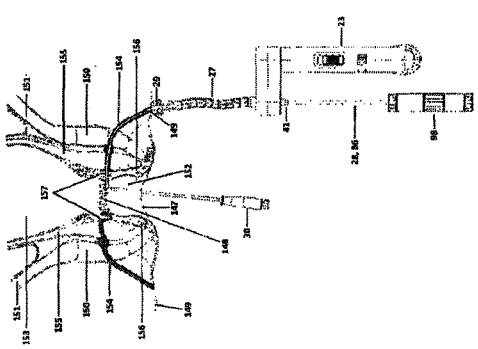
Figure 47:
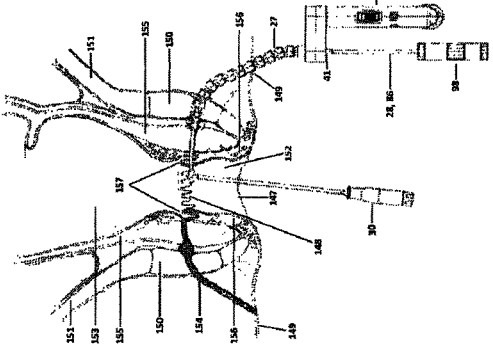

The movement providing and transmitting apparatus (23) is installed at the back of the movement carrier flexible guide (FIG. 44). The functional guide stretching and securing handle (98) is installed at the back of the functional guide (FIG. 45). The movement providing and transmitting apparatus is moved on the flexible shaft and in this manner the fistula is brought to the outer mouth and the motor is started (46). The fistulectomy operation is conducted by moving it from the outer mouth to the inner mouth (FIG. 47, 48). The movement transmitter flexible shaft system is removed out of the fistula by shifting it on the flexible guide (FIG. 49).

Figure 54:
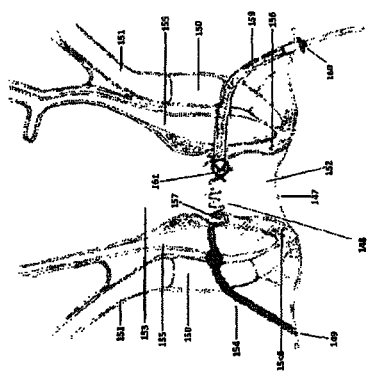
Figure 55:
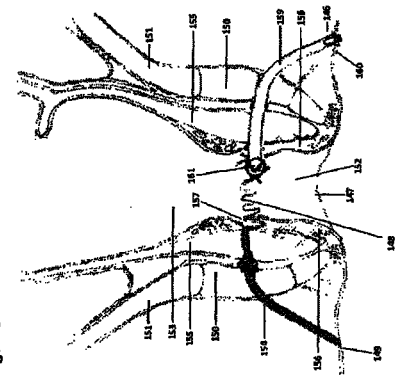
Figure 56:
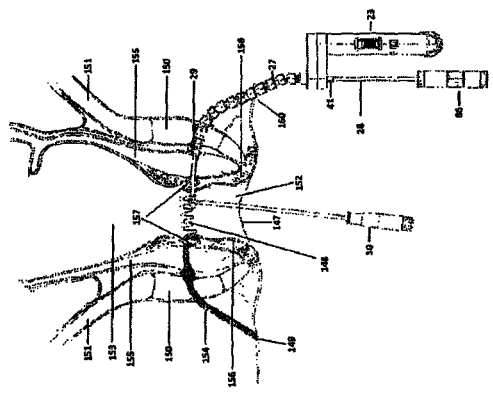
FIG. 56) shows the fistulectomy process in a transsphincteric fistula schematically.
Figure 57:
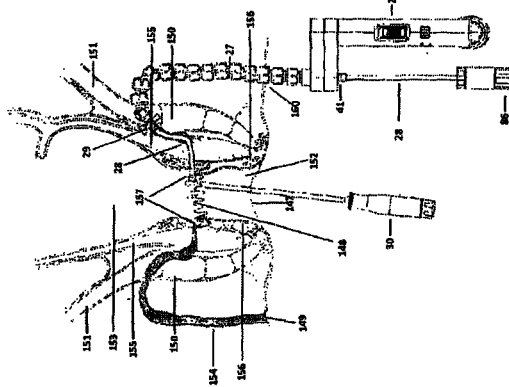
FIG. 57) shows the fistulectomy process in a suprasphincteric fistula schematically.
Figure 58:
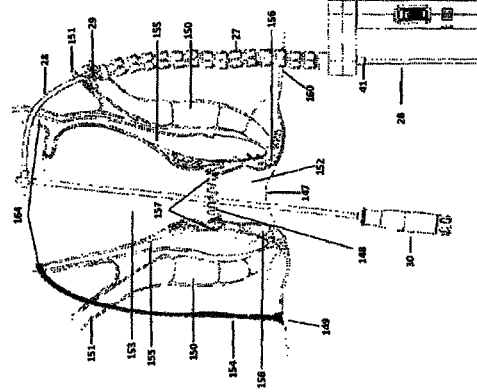
FIG. 58) shows the fistulectomy process in a extrasphincteric fistula schematically.

The guide tip holding and securing apparatus which holds the flexible shaft tip of the fistula trace in the anal channel is removed from the securing and stretching spring and movement provider and transmitter apparatus and functional guide (52) by the flexible shaft system (FIG. 50, 51). The guide is removed from the trace. After the fistulectomy, the inner mouth is stitched or closed with the help of the advancement flap (FIG. 53). The drain is placed in the fistula trace (FIG. 54). It is removed after 72 hours. The drain stabilizer remains on the tissue until it heals. The drain mouth closer is placed on top of it (FIG. 55).

REFERENCE NUMBERS AND CORRESPONDING PART DEFINITIONS:

I) CANNULATION GUIDE APPARATUS:

1) Cannulation guide apparatus
2) Handle part which contains the motor and the batter in the cannulation guide
3) Flexible guide system of the cannulation guide
4) Raindrop shaped tip of the cannulation guide
5) Bearing at the rear section of the cannulation guide (preventing the friction between the tip and the spring)
6) Flexible guide of the cannulation guide
7) Backside conical spring wrapping the flexible guide
8) Rectangular part which fixes the flexible guide to the moving part
9) Part securing the conical spring to the shaft
10) Upper part of the shaft to which part 9 is secured
11) Moving part converting and transferring the rotational movement from the motor to the flexible shaft
12) Cylindrical structure transferring the rotational movement from the motor to the moving party
13) Spring placed on the moving part
14) Bearing mounted on the movement transmitter
15) Bearing mounted on the moving party, installed and moving in a sinusoidal direction
16) Power switch
17) Electric motor
18) Battery
19) The back cover of the shaft
20) Gap in which the rectangular part of the flexible shaft is rested

REFERENCE NUMBERS AND CORRESPONDING
PART DEFINITIONS:

21) Sine-shaped surface on which the bearing mounted on the moving part turns
22) Projections providing vibration on sinusoidal curve

II) FISTULECTOMY SET:

23) Motion provider and transmitter apparatus
24) Handle-Shank containing the battery in the motion provider and transmitter apparatus
25) Handle portion- Mid-section containing the motor in the motion provider and transmitter apparatus
26) Movement transmitter front section of the motion provider and transmitter apparatus
27) Movement carrier flexible shaft
28) Functional guide (guide shaft)
29) Cutting unit (126, 132, 134, 137)
30) Clutch apparatus of the carrier functional guide tip
31) Speed adjustment button
32) Power switch
33) Direction selection switch
34) Gear with which the movement from the motor is transmitted
35) Top and bottom bearing on which the gear is secured
36) Belt transmitting movement between the two gears
37) Gear transmitting the rotational movement to the bearing flexible shaft
38) Bearing securing the gear (37) from the top and the bottom
39) Channel in the center of the gear
40) Spring and pin housing
41) Functional part transmitting the rotational movement to the flexible shaft
42) Pin
43) Spring
44) Guide securing the functional part to the gear
45) Bottom cover of the handle
46) Annular channel, the mid-section of which the handle is secured
47) Channel in which the pin and the spring is placed
48) Channel through which the cables pass through
49) Battery
50) Cylindrical structure at the center of which the handle is secured
51) Motor
52) Shaft (53) transmitting the rotational movement of the motor to the gear system
53) Cylinder secured in the middle portion of the front section
54) Cylinder secured in the middle portion of the front section
55) Spheroid slot in the mid-section into which the pin enters
56) Cylinder securing the mid-section to the handle
57) Annular channels in the outer surface of the cylinder (56)
58) Cavity into which the pin (47) enters
59) Pin
60) Spring pushing the pin
61) Space to pass the cables

III) PRACTICAL MOVEMENT PROVIDING AND TRANSMITTING APPARATUS:

62) Practical movement providing and transmitting apparatus - Handle portion
63) Power switch
64) Rear cover of the handle
65) Battery
66) Motor
67) Proximal gear
68) Top and bottom bearing of the proximal gear
69) Distal gear

REFERENCE NUMBERS AND CORRESPONDING
PART DEFINITIONS:

70) Top and bottom bearing of the distal gear
71) Transmitter belt
72) Channel through which the functional guide passes

IV) CARRIER GUIDES, PARTS HOLDING AN SECURING THE CARRIER GUIDES:

73) Hard guide
74) Softened front section of the hard guide
75) Hard part of the hard guide
76) Rigid and conventional guide handle
77) Conventional guide
78) Flexible section of the conventional guide
79) Three parts of the guide
80) Rigid part of the conventional guide
81) Spring wrapped in the flexible part of the conventional guide
82) Flexible wire with which the spring is wrapped in the conventional guide
83) Guide compressing pin of the guide handle
84) Spring controlling the tightening of (83)
85) Rear screw stretching (83)
86) Spring-wound functional guide
87) Flexible front part of the spring-wound functional guide
88) Mid-section of the functional guide
89) Secured rear part of the functional guide
90) Tip of the functional guide
91) The innermost flexible wire of the flexible portion of the functional guide
92) Spring wrapping the innermost flexible wire of the functional guide
93) a) Moving spring on (92)
b) Cannulated bearings lined up on (92)
94) Moving tube outside the mid-section (88)
95) Hard part of the mid-section in the moving tube
96) Mounted tube at the rear part of the flexible guide
97) Flexible front section of the bearing flexible shaft
98) Securing and stretching spring of the functional guide
99) Front clamps of (98)
100) Tightening screw of the rear clamp (99)
101) Screw moving (104) a, b
102) Rear clamp of (98)
103) Screw tightening the front clamp of (98)
104) a) Rear part to which the rear clamp is secured
b) Front part to which the rear clamp is secured
105) Guide tip holding and securing stamp
106) Tip of the guide tip holding and securing stamp
107) Mid-tube section of the guide tip holding and securing stamp
108) Rear section of the guide tip holding and securing stamp
109) Tube connecting the handle and the tip including the wire tightening the tip
110) Shaft passing through (109)
111) Part moving the wire
112) Rods moving (113) and (114) on the spring with the help of (111)
113) Part (112) is secured
114) Part pushing the spring back
115) Spring
116) Back cover

V) MOVEMENT CARRIER FLEXIBLE SHAFT:

117) Hexahedron spheroid units
118) Front section of the spheroid units
119) Neck section of the spheroid units
120) Hexahedron housing spheroid units form at the rear section

REFERENCE NUMBERS AND CORRESPONDING PART DEFINITIONS:

121) Channel of the spheroid units through which guide passes
122) Corresponding section of the spheroid units at the bottom where the corners meet
123) Spheroid protrusions which prevent the coming out after the installation of the spheroid
124) Rear section of the spheroid units

VI) CUTTING UNITS:

125) Parts connecting the cutting units to the shaft
126) Flat blades of the externally cutting units
127) Cutting portions of the externally cutting units
128) Tissue chippers of the cut openings
129) Neck portion of blade
130) Cylindrical structures the blades hold onto
131) Channels passing through the middle of the blade
132) Bell-mouths of the externally cutting units
133) Conical cutting units
134) Flat blades of the internally cutting units
135) Shaft in which the blades are installed
136) Cutting edges
137) Saw-tooth-shaped edges of the internally cutting ones
138) Saw-tooth-shaped cutter

VII) FISTULA DRAINAGE SYSTEM:

139) Fistula drainage system
140) Cylinder closing the drain securing part
141) Drain
142) Drain securing part
143) Fluted roller securing the drain to the drain securing part
144) Cover of (140)
145) Stitch holes to fix the drain securing part to the skin

VIII) DURING THE CONDUCT OF THE FISTULECTOMY PROCESS:

146) Hole through which the drain securing part passes
147) Entrance of the anus
148) Dentate line
149) Outer mouth of the fistula trace
150) External sphincter
151) M. Levator ani
152) Anal canal
153) Rectum
154) Fistula trace
155) Internal sphincter
156) Anal mucosa
157) Internal mouth of the fistula trace
158) Feeding catheter
159) Excised fistula traces
160) Outer mouth of the excised fistula
161) Inner mouth of the excised fistula
162) Pathological intestine
163) Cured intestine
164) Inner mouth of the supra sphincter fistula
165) Inner mouth of the pelvic inflammatory fistula

The invention claimed is:

1. Fistulectomy set for excising the traces of anal fistula comprising:

a movement providing and transmitting apparatus, a movement carrying flexible shaft and a guide shaft passing therethrough adapted to guide the movement carrying flexible shaft, wherein the movement providing and transmitting apparatus is adapted to provide movement to the movement carrying flexible shaft and comprises: an apparatus handle portion comprising a substantially cylindrical middle section containing an electric motor to provide the movement, and a rotatable front section rotatably mounted to the middle section at a front side thereof containing a functional part adapted to transmit the rotation movement produced by the electric motor at the mid-section to the movement carrying flexible shaft, wherein the movement carrying flexible shaft is mounted to the functional part and the apparatus handle portion is rotatable about the guide shaft, such that the apparatus handle portion is adjustable for left and right hand side use; and a cannulation guide for identifying a fistula trace, comprising an end portion being a shaft system having a flexible shaft, wherein the flexible shaft is adapted to rotate, vibrate and reciprocate simultaneously and a guide handle portion connected to the end portion and adapted to generate the movement of the flexible shaft, wherein the handle portion is provided with an electromotor having a rotational shaft, a cylindrical structure for transmitting a rotational movement of the rotational shaft, a moving part which is movable along the cylindrical structure against a backside conical spring wrapping the flexible shaft and transmits the rotational movement of the rotational shaft, a bearing attached to the moving part and mounted on a circular sinusoidal cam-shaped surface of the handle portion, and wherein the bearing is adapted to convert the rotational motion from the electromotor to rotation, vibration and reciprocating motion by rotating on the circular sine curve shaped structure of the sinusoidal cam shaped surface.

2. Fistulectomy set according to claim 1, wherein the movement carrying flexible shaft is characterized by a hinged spiral structure which has the ability to curl in all directions, formed in a predetermined length by adding a plurality of spheroid units in succession, moving depending on the guide's orientation on the guide shaft passing through a channel in the center consisting of a spheroid unit which carries the electromotive induced axial rotation from the functional part to a plurality of cutting units.

3. Fistulectomy set according to claim 1, wherein each of a plurality of spheroid units are elements each of which comprising: a front section formed from six spheroid surfaces, the front sections of which are cut, rear sections flattened and sides symmetrical, made up of a rear section comprising ellipsoid incisions which prevent the removal of an ellipsoid part at the lower ends of the surfaces and six concave surfaces, corresponding to a plurality of ellipsoid surfaces at the front section, designed in such a way that one spheroid unit can enter the rear section of the other; and a neck portion in the center which connects the front and the rear section including channels for the guide shaft to pass.

4. Fistulectomy set according to claim 1, comprising a cutting unit adapted to cut the tissue encountered externally and internally, provided with axial rotary movement of the flexible shaft and mounted to the tip of the movement carrying flexible shaft.

5. Fistulectomy set according to claim 1, wherein the guide shaft is selected from the functional flexible guide types that are hard and conventionally flexible.

6. Fistulectomy set according to claim 1, further comprising a carrier guide tip holding and securing apparatus comprising a tip adapted to hold and secure the tip of the guide shaft.

7. Fistulectomy set according to claim 1, further comprising a drain system adapted to be placed in the fistula trace comprising a drain, a drain securing part and a fluted roller securing the drain to the drain securing part and a cylindrical cover adapted to be placed instead of the fluted roller when the drain is pulled after fistulectomy.

8. Fistulectomy set according to claim 1, further comprising a guide tip clutch apparatus, a rigid and conventional guide securing guide handle and a functional flexible guide stabilizer and a stretching shaft.

9. Fistulectomy set according to claim 1, wherein the flexible shaft comprises a tracking part at a front end and a conical spring at a rear end adapted for transferring rotation, vibration and reciprocating movement simultaneously and to fix and control the tracking part.

10. Fistulectomy set according to claim 1, wherein the apparatus handle portion comprises further a rotatable shank mounted to the middle section substantially vertically to the longitudinal axis of the middle section.

11. Fistulectomy set according to claim 1, wherein the apparatus handle portion comprises further a channel at a second end portion opposite to the first end portion and wherein the channel and the functional part are adapted for passing the guide shaft therethrough.

* * * * *